(12) United States Patent
Honda (10) Patent No.: US 8,082,029 B2
(45) Date of Patent: Dec. 20, 2011

(54) ADJUSTABLE SENSORS FOR USE WITH EXERCISE APPARATUS

(75) Inventor: Edward Honda, Chicago, IL (US)

(73) Assignee: Brunswick Corporation, Lake Forest, IL (US)

( * ) Notice: Subject to any disclaimer, the term of this patent is extended or adjusted under 35 U.S.C. 154(b) by 1038 days.

(21) Appl. No.: 11/750,097

(22) Filed: May 17, 2007

(65) Prior Publication Data

US 2008/0287816 A1  Nov. 20, 2008

(51) Int. Cl.
*A61B 5/0402* (2006.01)
(52) U.S. Cl. .............................. 600/520; 482/54; 482/62
(58) Field of Classification Search .................. 600/520, 600/481, 382; 482/51–57
See application file for complete search history.

(56) References Cited

U.S. PATENT DOCUMENTS

| | | | |
|---|---|---|---|
| 4,319,581 A | 3/1982 | Cutter | |
| 5,403,254 A * | 4/1995 | Lundin et al. | 482/52 |
| 6,165,129 A * | 12/2000 | Bates | 600/481 |
| 6,485,396 B2 | 11/2002 | Stevens | |
| 7,775,942 B2 * | 8/2010 | Hildebrandt et al. | 482/62 |
| 2003/0171190 A1 * | 9/2003 | Rice | 482/57 |
| 2005/0164838 A1 | 7/2005 | Watterson et al. | |

* cited by examiner

*Primary Examiner* — Carl H Layno
*Assistant Examiner* — Paula J Stice
(74) *Attorney, Agent, or Firm* — Hanley, Flight & Zimmerman, LLC (57) ABSTRACT

Adjustable sensors for use with exercise apparatus are described. An example apparatus includes a support frame to assist a user in an exercise and a sensor integral with the support frame. The sensor is to detect a physiological condition of the user through physical contact with the user, and a position of the sensor is adjustable by the user.

21 Claims, 5 Drawing Sheets

ADJUSTABLE SENSORS FOR USE WITH EXERCISE APPARATUS

FIELD OF THE DISCLOSURE

The present disclosure relates to exercise equipment and, more particularly, to adjustable sensors for use with exercise apparatus.

BACKGROUND

Exercise machines intended to provide a cardiovascular workout often include a sensor or sensors capable of detecting, measuring, or monitoring a physiological condition of a user. One common method of measuring a physiological condition involves the placement of sensors on the exercise equipment in locations at which a user is likely to make contact with (e.g., grasp with a hand) the equipment. When contacted, the sensors detect a physiological signal (e.g., a pulse), which is then processed, analyzed, and, perhaps, displayed to the exerciser.

Exercise equipment is typically mass produced and, thus, not typically customized for individual users. As a result, an individual user may prefer one exercise machine over another based on the geometry, dimensions or, more generally, the configuration or structure of the exercise machine. Some exercise machines include adjustable features to accommodate the needs or preferences of individual users. However, the adjustments are not always sufficiently accommodating. For example, the angle at which an exerciser is forced to grasp sensors, such as those mentioned above, is typically not adjustable. As a result, grasping such sensors may lead to uncomfortable or awkward positions, particularly during exercise.

DETAILED DESCRIPTION

Figure 1:
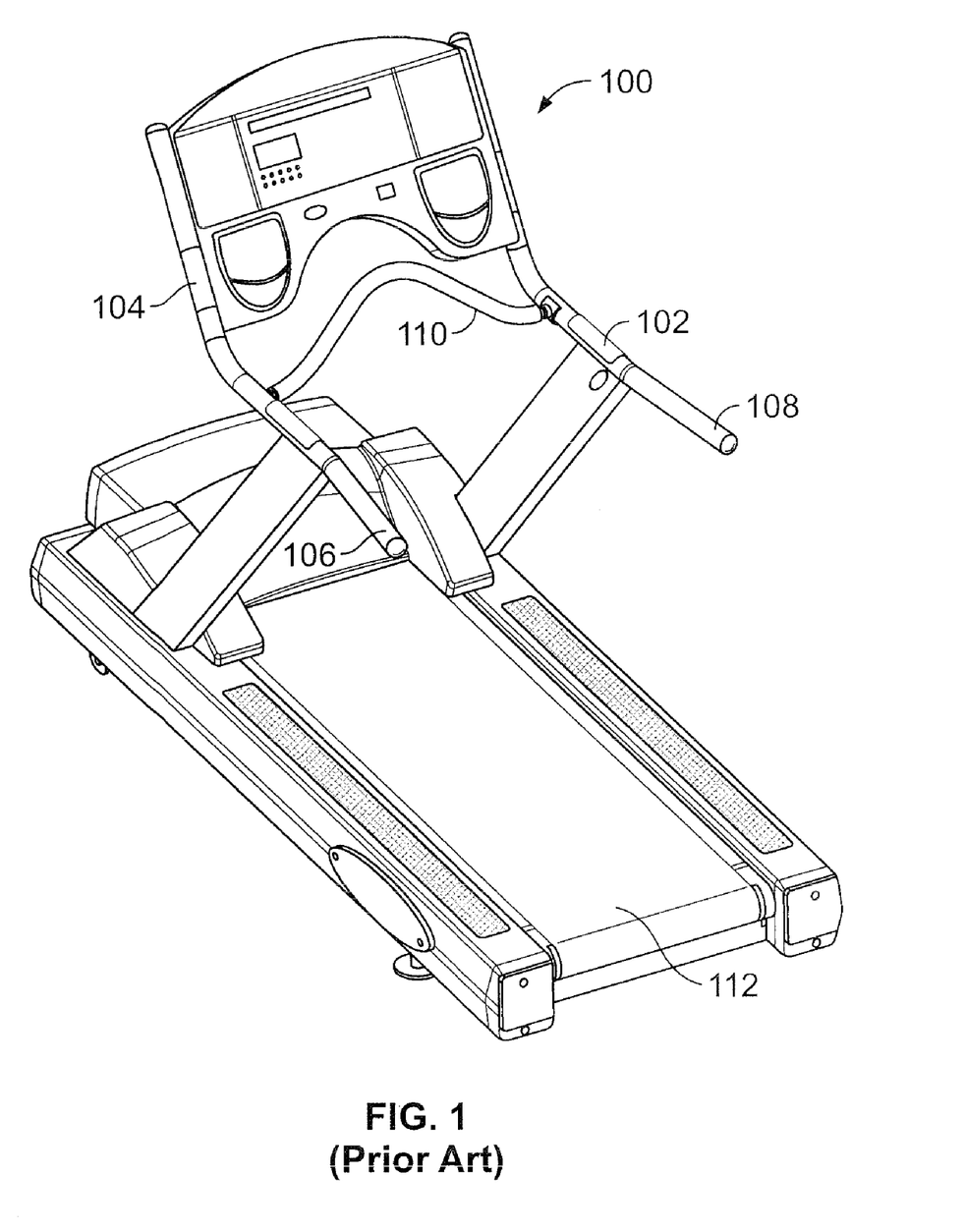
FIG. 1 depicts a known exercise machine having fixed sensor locations.

FIG. 1 depicts an example of a known exercise machine 100 that includes a sensor 102 to detect a physiological condition of a user. The exercise machine 100 includes a support frame 104 to aid a user in maintaining his or her balance, to provide a rest, or to otherwise allow the user to perform the exercise. While the support frame 104 can take any form, it typically includes a plurality of tubular bars adjacent to and/or surrounding the user. A common configuration for the support frame 104 is shown in FIG. 1. In particular, a first side bar 106 and a second side bar 108 extend along the sides of the exercise machine 100 perpendicular to a transverse front bar 110, which is positioned in front of a user of the exercise machine 100. While striding on a belt 112, the user can place his or her hands on any combination of the bars 106, 108, and 110 for support. To gather physiological information from the user, the sensor 102 is integrated into the support frame 104. The sensor 102 is located to accommodate a user's preferred hand placement on the support frame 104. In other example exercise machines, a sensor may be located where a user is required to grasp the structure to properly perform the exercise (e.g., the handle bars of an elliptical machine). While FIG. 1 depicts the example exercise machine 100 as a treadmill, a sensor such as the sensor 102 used to detect a physiological condition of a user may be implemented on a variety of different exercise machines (e.g., stationary bicycle machines, recumbent bicycle machines, stationary rowing machines, weight training machines, elliptical machines, etc.).

The sensor 102 depicted in FIG. 1 is fixed to the support frame 104 and is not adjustable by a user of the exercise machine 100. Varying heights, body types, and exercise styles of users result in an extensive set of possible user preferred sensor positions, all of which may not be sufficiently accommodated by such a non-adjustable sensor. More specifically, the inability to adjust the position of the sensor 102 relative to a user may not enable a user to achieve their preferred angle of contact with the sensor 102. For example, a user may not prefer the angle at which their wrist is positioned relative to their arm while contacting the sensor 102. Additionally or alternatively, a user may not prefer the angle at which their arm is positioned relative to their shoulder while contacting the sensor 102. Such awkward angles of contact with the sensor 102 can be eliminated by the example adjustable sensor described herein.

Figure 2:
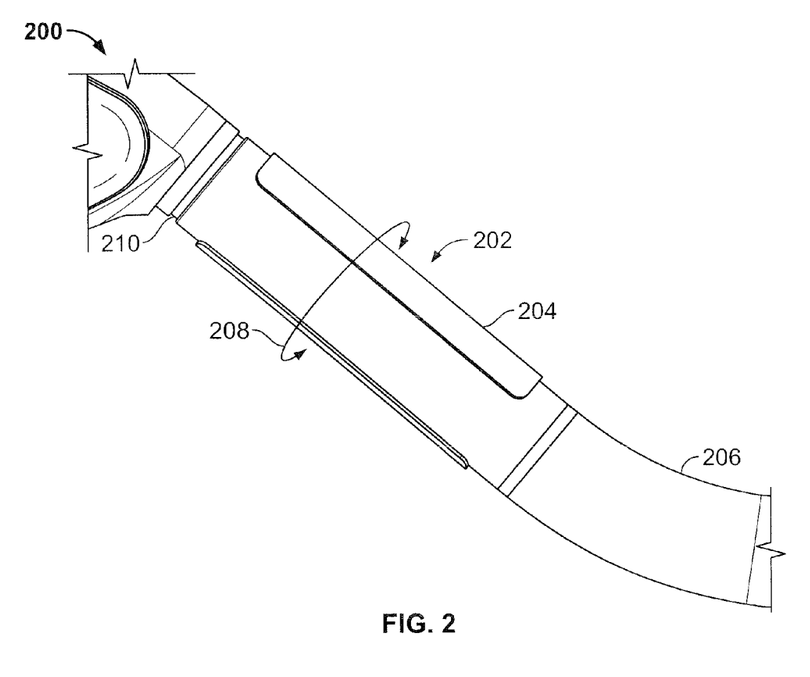
FIG. 2 illustrates an example adjustable sensor coupled to a portion of an exercise machine.

FIG. 2 depicts an example frame portion 200 of a support frame 206 (e.g., a handlebar or other frame portion) of an exercise machine (e.g., the exercise machine 100 of FIG. 1 or any other exercise machine) that includes an example adjustable sensor assembly 202. The adjustable sensor assembly 202 includes a sensor 204 (e.g., a metal electrode) to measure, detect, or monitor a physiological condition (e.g., a heart rate) of a user. The sensor 204 detects physiological signals (e.g., electrical voltages or potentials) generated by a user through physical contact with the user's skin. Upon the detection of a physiological signal (e.g., a pulse from a person using an exercise machine), the sensor 204 generates a corresponding electrical output, which may be sent to a processing system or unit (e.g., a processing unit 500 described below in connection with FIG. 5). For example, the sensor output may be routed through the support frame 206 to a processing unit that is connected to the support frame 206. However, the detection is usually performed in a noisy environment, as the human body produces many other signals corresponding to different bodily functions. For example, the contraction of muscles, which occurs frequently during exercise, produces a type of noise through which the physiological condition (e.g., a heart rate) is detected. Therefore, the initial or raw output of the sensor 204 is composed of multiple signals. To extract a desired physiological condition signal (e.g., a pulse signal), the initial output of the sensor 204 is processed further. In general, the output of the sensor 204 is filtered and amplified. However, one particular manner that may be used to process the output of the sensor 204 is described in U.S. Pat. No. 5,365,934, which is incorporated herein by reference in its entirety.

After conditioning and/or processing, the information associated with the sensor 204 may be utilized in a number of ways. For example, the physiological condition information (e.g., a pulse or heart rate) may be sent to a display unit (e.g., a display unit 501 described below in connection FIG. 5) to be displayed numerically and/or graphically. The exercise machine may automatically alter its operation (e.g., change a speed and/or load) based on the physiological information. Where the information associated with the sensor 204 includes a heart rate, a comparison may be made between the information generated by the sensor 204 and a predetermined target heart rate. Any results from such operations may be displayed to the user. Of course, the information associated with the sensor 204 may be utilized in other ways, as the foregoing are merely examples.

As mentioned above, the sensor assembly 202, including the sensor 204, is integrated into the support frame 206 (as described further in connection with FIGS. 3A-3D) of an exercise machine and may be located in a position in which a user is likely to make contact with the support frame 206. To accommodate users' individual preferences and/or needs, the sensor assembly 202 is rotatably adjustable as indicated by the curved arrow 208 in FIG. 2. As a result, each user can choose or select their preferred angle of contact with the sensor 204, thereby accommodating the preferences and/or needs of different users having different heights, body types, and/or running or walking styles. Such adjustability minimizes or eliminates awkward positions that users may otherwise experience when utilizing the sensor 204 to detect or monitor a physiological condition during exercise. For example, where a user's angle of contact with the sensor 204 is awkward such that their hands are rotated above their wrists (e.g., for a user of above average height), the user may rotate the sensor assembly 202 away from his or her body (i.e., clockwise) to more easily grasp the sensor 204.

FIGS. 3A-3D illustrate an example adjustment mechanism or assembly 300 that may be used to implement the example adjustable sensor 200 of FIG. 2. In this example, the adjustment mechanism 300 may provide a series or plurality of fixed or locked positions. Specifically, the example assembly or mechanism 300 provides a fixed range of rotational adjustment (e.g., 50 degrees) and a plurality of (e.g., five) predetermined intermediate positions within the fixed range. In other examples, alternative ranges of adjustment and/or numbers of predetermined intermediate positions within the adjustment range may be used instead. Further, another example adjustment assembly may be continuously rotatably adjustable around a support frame (i.e., without predetermined locking positions) to provide an unrestricted rotatable adjustment within a range of rotational adjustment.

Figure 3A:
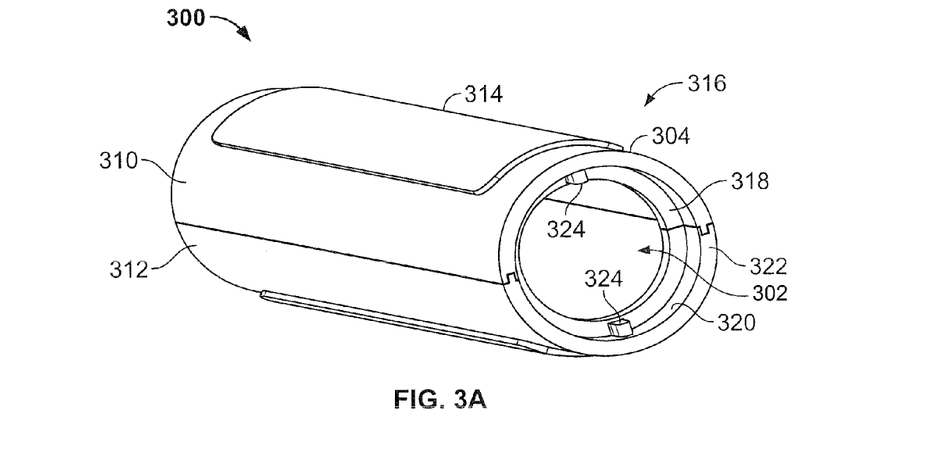
FIGS. 3A-3D illustrate an example adjustment mechanism that may be used to implement the example adjustable sensor of FIG. 2.
Figure 3B:
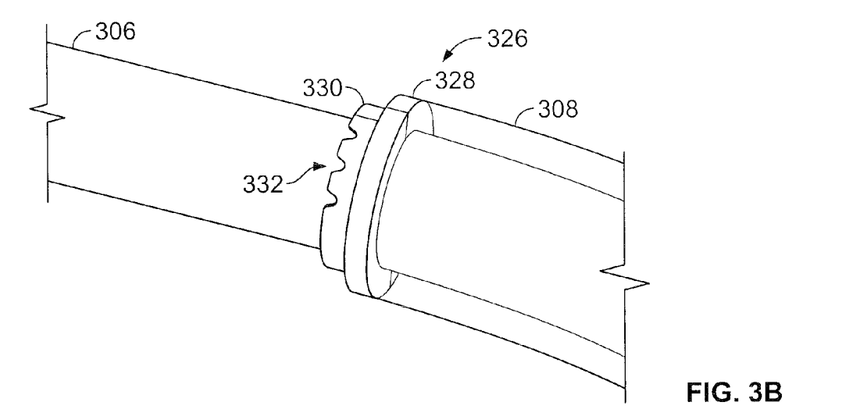
Figure 3C:
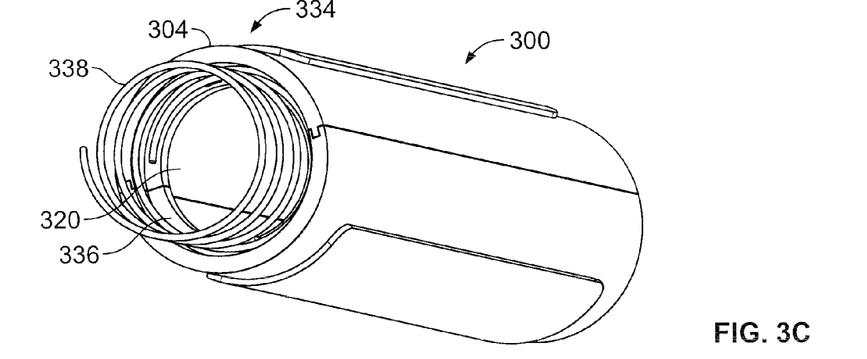
Figure 3D:
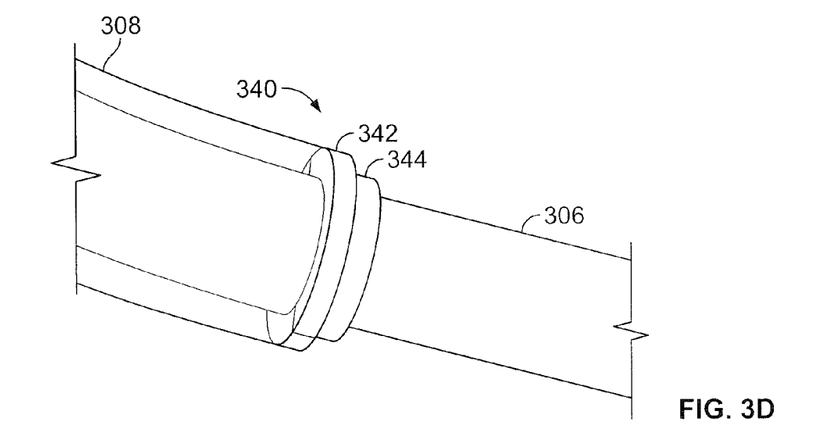

The example assembly 300 illustrated in FIGS. 3A and 3C includes an aperture 302 surrounded by an outer shell 304 to encase a portion 306 (e.g., a tubular bar) of a support frame 308 (FIGS. 3B and 3D). The assembly 300 may be molded as a unitary body, formed from two interlocking halves or portions, or otherwise constructed using known methods. By way of example, FIG. 3A shows the outer shell 304 formed from an upper half cylinder 310 and a lower half cylinder 312. The half cylinders 310 and 312 may be configured to interlock to enable the assembly 300 to be installed or attached to the portion 306 of the support frame 308 and/or to enable the assembly 300 to be disassembled for maintenance, replacement, inspection, etc. Additionally, one or more sensors 314 (e.g., electrodes) may be placed on the outer surface of the assembly 300 to detect or monitor a physiological condition of a user.

At one end portion 316 (FIG. 3A) of the assembly 300, a shoulder 318 extends from an inner surface 320 of the outer shell 304 to provide an annular face or surface within the assembly 300. The shoulder 318 is recessed within the outer shell 304 to leave a portion of the inner surface 320 exposed between the shoulder 318 and an end 322 of the assembly 300. Teeth or protrusions 324 having a substantially similar thickness as the shoulder 318 (i.e., extending a substantially similar distance from the outer shell 304) may be disposed against the inner surface 320 between the shoulder 318 and the end 322. For example, the teeth or protrusions 324 may be molded to the end of the inner surface 320 and/or the face of the shoulder 318. While FIG. 3A shows two teeth or protrusions 324, the assembly 300 may include more or less teeth or protrusions 324 to accommodate design preferences. Further, while FIG. 3A shows the teeth or protrusions 324 spaced approximately 180 degrees apart along the shoulder 318, other examples may include teeth or protrusions in alternative arrangements (e.g., 90 degrees apart).

The teeth or protrusions 324 are configured to engage a receiving portion 326 shown in FIG. 3B. The receiving portion 326 includes a first substantially circular member or ring 328 having an outer diameter substantially equal to the outer diameter of the outer shell 304 of FIG. 3A. The receiving portion 326 also includes a second substantially circular member or ring 330, which may be integrally formed with the ring 328, having an outer diameter substantially equal to the outer diameter of the annular shoulder 318 of FIG. 3A. The ring 330 includes a plurality of (e.g., three) grooves or notches 332 configured (i.e., shaped or molded) to receive the teeth or protrusions 324. Where the assembly 300 includes two or more teeth or protrusions 324, the receiving portion 326 may include a matching set of grooves or notches (not shown) on the opposite side of the ring 330 (e.g., positioned 180 degrees around the receiving portion 326 from the grooves or notches 332). In use, the assembly 300 is placed over the portion 306 of the support frame 308 to align the teeth or protrusions 324 with the notches 332. Thus, the engagement of the teeth or protrusions 324 within the notches 332 allows the assembly 300 to be fixed or retained in predetermined angular or rotational positions.

FIG. 3C shows another end portion 334 of the assembly 300. Similar to the configuration of the end portion 316, a shoulder 336 extends from the inner surface 320 of the outer shell 304 to create an annular face or surface within the assembly 300. The shoulder 336 is recessed within the outer shell 304 to provide an interface or seat for a spring 338 having an outer diameter slightly smaller than an inner diameter of the outer shell 304. In other words, the spring 338 is configured to surround the portion 306 of the support frame 308 and to engage a receiving portion of the support frame 308. For example, FIG. 3D shows an example receiving portion 340 similar to the receiving portion 326 of FIG. 3B. The receiving portion 340 includes a first substantially circular member or ring 342 having an outer diameter substantially equal to the outer diameter of the outer shell 304 of the assembly 300. Further, the receiving portion 340 includes a second substantially circular member or ring 344, which may be integrally formed with the ring 342, having an outer diameter substantially equal to the outer diameter of the shoulder 336 of the assembly 300. The spring 338 engages and is compressed between the ring 342 of the receiving portion 340 and the shoulder 336, thereby creating an opposing force between the two surfaces.

Thus, the spring 338 provides a force to maintain the engagement between the teeth or protrusions 324 and the notches 332 described in FIGS. 3A and 3B. Referring back to FIG. 2, which shows a sensor assembly 202 in a predetermined position (e.g., locked in a fixed position via the teeth or protrusions 324 and notches 332 described above), a gap 210 allows a user to compress the spring 338 (FIG. 3C) by shifting the sensor assembly 202 to close the gap 210. Such movement of the sensor assembly 202 withdraws the teeth or protrusions 324 from the notches 332 and allows the sensor assembly 202 to be rotated relative to the support frame 206. If a user releases the sensor assembly 202 in a position in which the teeth or protrusions 324 are aligned with a space between the notches 332, the sensor assembly 202 will remain in an unlocked position. However, when the teeth or protrusions 324 are aligned with the notches 332 (e.g., a user shifts the assembly 202 to a position to accommodate a preference for sensor positioning), the spring 338 forces the teeth or protrusions 324 (along with the entire sensor assembly 202) toward the receiving portion 326 and into the notches 332, thereby locking the sensor assembly 202 into position and re-exposing the gap 210.

The presence or absence of the gap 210, indicates whether the sensor assembly 202 is fixed in one of the predetermined positions or between one of the predetermined positions (i.e., in an unfixed or unlocked position). For example, the status (e.g., whether the sensor assembly 202 is in a fixed position and, if so, which predetermined position) of the sensor assembly 202 may be shown by including different colors that are uncovered or revealed according to the position status of the sensor assembly 202. A first color (e.g., green) may be revealed (e.g., a colored outer surface of the ring 344 of the receiving portion 340 is exposed) when the sensor assembly 202 is locked in a predetermined position. In other words, when the gap 210 is exposed or present, a color indicating a locked position may be presented to the user. When the sensor assembly 202 is in between predetermined positions (i.e., unlocked), only a second color (e.g., black or red) is displayed (e.g., the outer shell 304 of FIGS. 3A and 3B blocks the colored surface of the ring 344 of the receiving portion 340). This is merely one example method of indicating the status of the sensor assembly 202, as other suitable methods may be implemented.

The number of notches 332 combined with the space provided between each of the notches 332 determines the range of adjustability and number of predetermined positions provided by the sensor assembly 202. In one example, the sensor assembly 202 may incorporate a fifty degree range of adjustment with three predetermined positions throughout the range adjustment (i.e., two end positions and one intermediate position). By way of example, such an example sensor assembly is initially in a neutral, or center position (e.g., a position determined as a common user preferred position). The example sensor assembly may then be rotated to a forward position in which the sensor of the example sensor assembly is adjusted (e.g., rotated) twenty-five degrees from the neutral or center position toward a user. The example sensor assembly may alternatively be shifted to a position in which the sensor of the example sensor assembly is adjusted twenty-five degrees from the neutral position away from the user. Alternatively, as mentioned above, another example sensor assembly may include an unrestricted continuous range of adjustment with or without any predetermined or fixed positions.

While the example assembly 300 is illustrated and described above as formed from two interlocking half cylinders 310 and 312, another example assembly may be formed as a unitary molded body, including internal shoulders that perform the function of the shoulders 318 and 336 described above. Alternatively, internal shoulders may be formed via an inner concentric cylinder extending from a portion of the inner surface of an outer concentric cylinder (e.g., the outer shell 304 of FIGS. 3A and 3C). The two ends of such an inner concentric cylinder may form the internal shoulders to engage receiving portions of the support frame (e.g., the receiving portion 326 and 340 of FIGS. 3B and 3D). Further, another example assembly may include a casing (e.g., a cup) disposed within the assembly to house a spring (e.g., the spring 338 of FIG. 3C). For example, in FIG. 3C, a metal or plastic cup (not shown) having a slightly smaller diameter than the inner diameter of the outer shell 304 may be disposed within the assembly 300 to encase the spring 338. Additionally or alternatively, such a casing or cup may be fixed to the inner surface 320 of the outer shell 304 and positioned to receive the support frame portion 306, thereby replacing (i.e., eliminating the need for) the shoulder 336. In other words, the casing or cup may act as the interface or seat for the spring 338 otherwise provided by the shoulder 336.

Further, while FIGS. 3A and 3B show the teeth or protrusions 324 on the assembly 300 and the notches 332 on the receiving portion 326, an inverse arrangement is possible. For example, the receiving portion 326 may include teeth or protrusions and the assembly 300 (specifically, the shoulder 318) may include grooves or notches. An assembly with such a configuration functions in a similar manner as the assembly 300 described above.

Figure 4A:
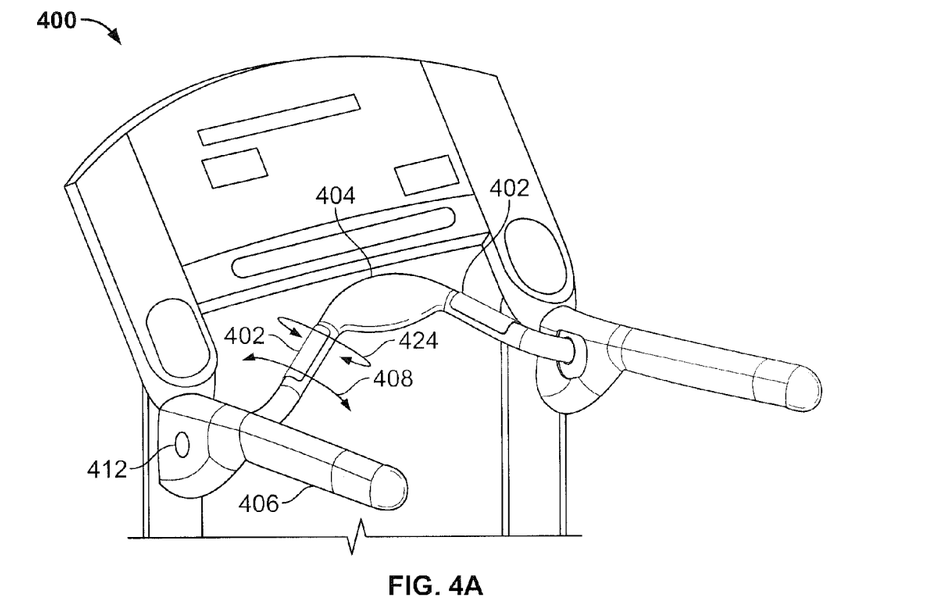
FIG. 4A illustrates another example adjustable sensor coupled to an adjustable portion of an exercise machine.

FIG. 4A illustrates an example exercise machine 400 having a sensor(s) 402 (e.g., an electrode) that may be used to detect or monitor a physiological condition (e.g., a heart rate) located on an example adjustable bar 404 of a support frame 406. As stated above, given the wide range of possible user heights, body types and exercise styles, a non-adjustable sensor (e.g., the sensor 102 of FIG. 1) may be incapable of accommodating many individual user preferences or needs. A user may prefer to alter the position of a portion (e.g., a section of a support frame) of an exercise machine. For example, the front bar 110 in FIG. 1 may be too high for a short user and too low for a tall user. Alternatively, a user with a certain running style may not prefer the position of (e.g., their angle of contact with) the front bar 110. With known exercise equipment such as that shown in FIG. 1, if a user prefers to use a sensor located on such a portion of the support frame, they may be forced into an awkward position, which may discourage use of the sensor, cause inaccurate readings, and/or create a general non-preference for the exercise machine.

The example adjustable bar 404 illustrated in FIG. 4A enables a user to alter the angle of contact made (e.g., through physical contact with a user's hand) with the sensor(s) 402 located on the adjustable bar 404. While FIG. 4A shows the exercise machine 400 as a treadmill, the adjustable bar 404 described herein may be implemented on a variety of exercise machines (e.g., stationary bicycle exercise machines, recumbent bicycle machines, stationary rowing machines, weight training machines, stationary stair climbing machines, etc.). As indicated by an arrow 408 in FIG. 4A, the adjustable bar 404 may be moved forward or backward, relative to the user. For example, a user of shorter than average height may adjust the bar 404 (and therefore the sensor(s) 402) towards his or her body to avoid an awkward angle of contact with the sensor(s) 402.

Figure 4B:
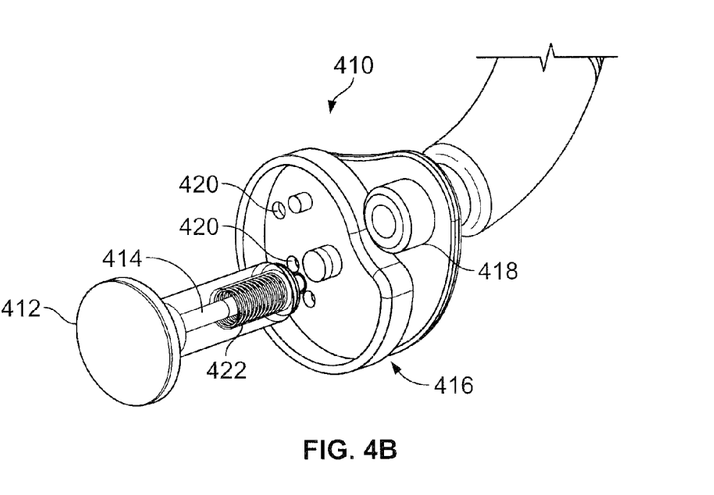
FIG. 4B illustrates an example adjustment mechanism that may be used to implement the example adjustable sensors of FIG. 4A.

FIG. 4B illustrates an example mechanism 410 to enable the adjustment described above in connection with FIG. 4A. In this example, a knob or button 412 (also shown in FIG. 4A) allows a user to utilize the mechanism 410. The button 412 may be positioned on an accessible area of the support frame 406 (e.g., on the outside surface of a handrail that may be easily reached). The button 412 is coupled to a shaft, pin, or rod 414 that passes through the support frame 406 to engage a plate 416. The plate 416 may be disposed within (i.e., encased by) the support frame 406 and configured to receive both the rod 414 and an end 418 of the adjustable bar 404. In other words, the plate 416 facilitates a manipulation of the adjustable bar 404 via the button 412.

The plate 416 includes a plurality of apertures or holes 420 to receive the rod 414. The apertures 420 function in a similar manner to the notches 332 of FIG. 3B in that the apertures 420 define a set of fixed or locked positions for the adjustable bar 404. In use, the button 412 may be pulled outward (i.e., away from the support frame 406), thereby disengaging the rod 414 from one of the apertures 420. In this example, the user overcomes a force created by a spring 422 that maintains the engagement between the rod 414 and one of the apertures 420. While the button 412 is pulled outwardly and held to disengage to the rod 414 from the apertures 420, the user may adjust (e.g., alter the angle of contact with the sensor(s) 402) the adjustable bar 404 to conform to their preference. When the preferred angle of contact is achieved the button 412 may be released to lock the adjustable bar 404 in one of the fixed positions (i.e., one of the apertures 420). As long as the rod 414 is engaged with one of the apertures 420, the adjustable bar 404 remains securely locked in place.

The adjustable bar 404 may incorporate a fixed range of adjustment and a plurality of predetermined positions throughout the fixed range. For example, a fifty degree range of adjustment with three predetermined positions throughout the range of adjustment may be provided. In this case, the example adjustable bar 404 may initially be in a neutral, or center position (e.g., a position determined as the most likely user preferred position). In another position, the example adjustable bar 404 may be moved to a position in which the sensor of the example adjustable portion is adjusted twenty-five degrees from the neutral position toward a user. In another position, the example adjustable bar 404 may be moved to a position in which the sensor of the example adjustable portion is adjusted twenty-five degrees from the neutral position away from the user. Alternate ranges of adjustment and predetermined intermediate and end positions may be employed. Another example adjustable portion may include an unrestricted range of adjustment with or without any predetermined intermediate positions. Such an example may use a frictional force to retain a position or may allow the bar to move freely (i.e., a user may hold the bar in place).

While the sensor(s) 402 of FIG. 4A is illustrated and described above as fixed to the adjustable bar 404, in another example, the example assemblies 202 and 300 illustrated in FIGS. 2 and 3A-3D, respectively, may be implemented on the adjustable bar 404 illustrated in FIGS. 4A and 4B. For example, the portion 200 of the support frame 206 shown in FIG. 2, including the sensor 204, may be adjustable, similar to the adjustable portion 404 of FIGS. 4A and 4B. As further illustration, in FIG. 4A, an adjustable sensor assembly (e.g., the sensor assembly 300 described in FIGS. 3A-3D) may be used to implement the sensor(s) 402 on the adjustable bar 404. The sensor assembly may be rotated around the adjustable bar 404, as indicated by an arrow 424. Further, as described above, the adjustable bar 404 may be moved forward or backward relative to the user of the exercise machine. Such a combination accommodates a wider variety of preferences by creating more possible angles of contact for a user utilizing a sensor to detect or monitor a physiological condition.

The improved ability of a user to comfortably grasp the sensors described herein provides multiple benefits. For example, many of the sensors used on exercise machines require a certain amount or area of exposure to obtain an accurate reading. Therefore, detection or monitoring accuracy increases with a greater surface area of skin making contact with the sensor. In other words, adjustable sensor positions provide the user greater exposure to the sensor, allowing for substantially improved contact with the user's hands. Moreover, as a user finds it easier to grasp a sensor, he or she may be more likely to maintain stable contact with the sensor. The user is also more likely to prefer an exercise machine with greater flexibility over one that forces him or her into awkward, strenuous positions for the duration of an exercise session.

Figure 5:
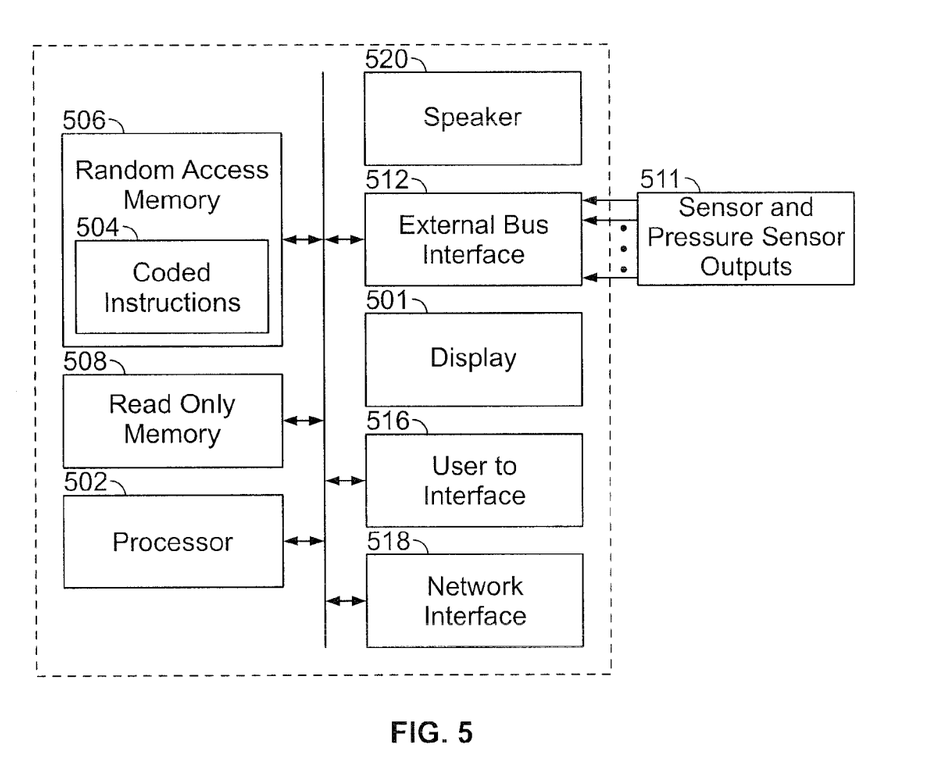
FIG. 5 illustrates an example manner of implementing an example processor and display unit.

Furthermore, regardless of the type or combination of adjustable sensors implemented on an exercise machine, each sensor may be operatively connected (e.g., routed through the support frame 206 of FIG. 2) to a processing unit or system (e.g., the processing unit 500 of FIG. 5) which, in turn, may be in communication with a display unit (e.g., the display unit 501 of FIG. 5). The display unit may present the user with exercise parameters, results, options, etc. The display unit also may present the information associated with the sensor (e.g., a heart rate detected by the sensor 204 of FIG. 2). The output of the sensor may be processed and analyzed by the processing unit and then communicated to the display unit. The data may be displayed in a variety of arrangements, for example, graphically or numerically.

FIG. 5 is a schematic diagram of an example manner of implementing an example processor and display unit. To process and analyze the information generated by the sensors 202, the example processor and display unit 500 of FIG. 5 includes a general purpose programmable processor 502. The example processor 502 executes coded instructions 504 present in a main memory (e.g., within a random access memory (RAM) 506 as illustrated and/or within a read only memory (ROM) 508). The example processor 502 may be any type of processing unit, such as a microprocessor from the AMD®, Sun® and/or Intel® families of microprocessors. The example processor 502 may execute, among other things, machine accessible instructions to perform the example process of FIG. 4 and/or the other processes described herein.

The example processor 502 is in communication with the example main memory (including the ROM 508 and the RAM 506) via a bus 510. The example RAM 506 may be implemented by dynamic random access memory (DRAM), Synchronous DRAM (SDRAM), and/or any other type of RAM device, and the example ROM 508 may be implemented by flash memory and/or any other desired type of memory device. Access to the example memories 508 and 506 may be controlled by a memory controller (not shown) in a conventional manner.

To receive sensor output signals, the example processor and display unit 500 includes any variety of conventional interface circuitry such as, for example, an external bus interface 512. For example, the external bus interface 512 may provide one input signal path (e.g., a semiconductor package pin) for each sensor. Additionally or alternatively, the external bus interface 512 may implement any variety of time multiplexed interface to receive output signals from the sensors via fewer input signals.

To display information for viewing by an exerciser or personal trainer, the example processor and display unit 500 includes any variety of display 501 (e.g., a liquid crystal display screen). To allow an exerciser to be identified, the example processor and display unit 500 includes any variety of user identification interface 516. Example interfaces 516 include a keypad, a radio frequency identification (RFID) tag reader, a universal serial bus (USB) memory interface, etc. For example, an exerciser may identify themselves by passing an associated device containing an RFID tag (e.g., a membership card) near an RFID tag reader 516. When the membership card is detected and/or identified by the RFID tag reader 516, the example RFID tag reader 516 provides to the example processor 502, for example, the exerciser's identification number (e.g., membership number) read and/or otherwise determined from the membership card.

To allow the example processor and display unit 500 to interact with a remote server, the example processor and display unit 500 includes any variety of network interfaces 518 such as, for example, a wireless LAN interface in accordance with, for instance, the Institute of Electronics and Electrical Engineers (IEEE) 802.11b, 802.11g, 802.15.4 (a.k.a. ZigBee) etc. standards. The example processor 502 may use the example network interface 518 to obtain target exercise parameters for an identified user and/or to provide exercise parameters determined while the identified user exercises.

To allow the example processor and display unit 500 to generate sounds, the example processor and display unit 500 includes any variety of speaker 520. The example processor 502 can cause any variety of sounds such as, for example, a user's current heart rate, to be produced by the example speaker 520 while a user is exercising.

Although an example processor and display unit 500 has been illustrated in FIG. 5, processor and display units may be implemented using any of a variety of other and/or additional devices, components, circuits, modules, etc. Further, the devices, components, circuits, modules, elements, etc. illustrated in FIG. 5 may be combined, re-arranged, eliminated and/or implemented in any of a variety of ways.

Although certain example methods and apparatus have been described herein, the scope of coverage of this patent is not limited thereto. On the contrary, this patent covers all methods and apparatus fairly falling within the scope of the appended claims either literally or under the doctrine of equivalents.

What is claimed is:

1. An exercise apparatus comprising:
    a support frame including a rotatable adjustment mechanism; and
    a sensor assembly comprising an aperture configured to receive a segment of the support frame, a sensor configured to detect a physiological condition of a user through direct physical contact with the user, and an element to engage the adjustment mechanism such that a position of the sensor relative to the segment of the support frame received by the sensor assembly is rotatably adjustable by the user.

2. The apparatus as defined in claim 1, further comprising a processor system.

3. The apparatus as defined in claim 2, wherein the processor system is to cause the display of information associated with the physiological condition.

4. The apparatus as defined in claim 1, wherein the position of the sensor is adjustable to a plurality of fixed positions.

5. The apparatus as defined in claim 4, further comprising a first indicator on the sensor assembly to be visible when the sensor is in one of the fixed positions and a second indicator to block visibility of the first indicator when the sensor is not in one of the fixed positions.

6. The apparatus as defined in claim 5, wherein the first indicator is a first color and the second indicator is a second color.

7. The apparatus as defined in claim 1, the wherein the element comprises a protrusion to engage the adjustment mechanism of the support frame to fix the position of the sensor in one of a plurality of predetermined positions.

8. The apparatus as defined in claim 1, wherein the position of the sensor is adjustable by rotating the sensor assembly about the segment of the support frame received by the aperture of the sensor assembly.

9. The apparatus as defined in claim 1, wherein the sensor comprises an electrode and the physiological condition comprises a heart rate.

10. The apparatus as defined in claim 1, wherein the adjustment mechanism is positioned at a junction of a first portion of the support frame having a first outer diameter and a second portion of the support frame having a second outer diameter, the first outer diameter being greater than the second outer diameter.

11. An exercise apparatus comprising:
    a frame including a first portion to be grasped by a user and a second portion having an adjustment mechanism to receive a sensor assembly, the sensor assembly comprising an aperture configured to receive the second portion of the frame, the sensor assembly further comprising a sensor configured to detect a physiological condition of the user, wherein a position of the sensor relative to the second portion of the frame is rotatable around the frame via the adjustment mechanism of the frame.

12. The exercise apparatus as defined in claim 11, further comprising a processor system.

13. The exercise apparatus as defined in claim 12, wherein the processor system is to cause the display of information associated with the physiological condition.

14. The exercise apparatus as defined in claim 11, wherein the position of the sensor is rotatable to a plurality of predetermined positions.

15. The exercise apparatus as defined in claim 14, further comprising a first indicator on the sensor assembly to be visible when the sensors are in one of the fixed positions and a second indicator to block visibility of the first indicator when the sensors are not in one of the fixed positions.

16. The exercise apparatus as defined in claim 15, wherein the first indicator is a first color and the second indicator is a second color.

17. The exercise apparatus as defined in claim 11, wherein the sensor assembly comprises a mechanism having a protrusion to selectably engage a plurality of positioning elements of the adjustment mechanism of the frame.

18. The exercise apparatus as defined in claim 11, wherein the sensor comprises an electrode and the physiological condition comprises a heart rate.

19. An exercise apparatus comprising:
    a sensor to detect a physiological condition of a user through physical contact with the user; and
    an assembly including a first portion and a second portion, the first and second portions encasing a segment of a support frame, wherein the sensor is on an outer surface of the first portion of the assembly; and
    an adjustment element configured to selectably engage an adjustment mechanism integral with the support frame in order to adjust a position of the sensor relative to the segment of the support frame encased by the sensor assembly, wherein the assembly is configured to rotate about the support frame to adjust the position of the sensor.

20. The apparatus as defined in claim 19, further comprising a first indicator to be visible when the sensor is in one of a plurality of fixed positions and a second indicator to become visible when the sensor is not in one of the fixed positions, wherein the first indicator is different from the second indicator.

21. The apparatus as defined in claim 20, wherein the first indicator is a first color and the second indicator is a second color.

* * * * *